United States Patent
Ramamurthy

(10) Patent No.: US 8,137,535 B2
(45) Date of Patent: Mar. 20, 2012

(54) METHOD FOR ADJUSTING CATALYST ACTIVITY

(75) Inventor: Pritham Ramamurthy, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 752 days.

(21) Appl. No.: 12/021,348

(22) Filed: Jan. 29, 2008

(65) Prior Publication Data

US 2009/0192338 A1  Jul. 30, 2009

(51) Int. Cl.
*C10G 11/05* (2006.01)

(52) U.S. Cl. ............ 208/120.35; 208/119; 208/120.01; 208/120.25; 208/122; 208/124

(58) Field of Classification Search ............... 208/106, 208/113, 118, 119, 121, 122, DIG. 2, 124, 208/120.35, 120.01, 120.25; 502/514
See application file for complete search history.

(56) References Cited

U.S. PATENT DOCUMENTS

| | | | | |
|---|---|---|---|---|
| 3,926,781 A | * | 12/1975 | Gale | 208/117 |
| 3,972,832 A | * | 8/1976 | Butter et al. | 502/77 |
| 4,118,339 A | * | 10/1978 | Latos | 502/27 |
| 4,175,057 A | * | 11/1979 | Davies et al. | 502/61 |
| 4,309,309 A | * | 1/1982 | Blanton, Jr. | 502/42 |
| 4,350,614 A | * | 9/1982 | Schwartz | 502/74 |
| 4,377,494 A | * | 3/1983 | Bertus et al. | 502/33 |
| 4,415,440 A | * | 11/1983 | Roberts et al. | 208/120.2 |
| 5,149,679 A | * | 9/1992 | Price et al. | 502/61 |
| 5,324,416 A | * | 6/1994 | Cormier et al. | 208/113 |
| 5,846,403 A | * | 12/1998 | Swan et al. | 208/113 |
| 6,159,887 A | * | 12/2000 | Trujillo et al. | 502/64 |
| 6,222,087 B1 | * | 4/2001 | Johnson et al. | 585/651 |
| 6,617,275 B1 | * | 9/2003 | Sharma et al. | 502/61 |
| 6,835,863 B2 | * | 12/2004 | Chester et al. | 585/651 |
| 6,936,239 B2 | | 8/2005 | Rao | |
| 6,964,934 B2 | | 11/2005 | Brady et al. | |
| 6,969,692 B2 | | 11/2005 | Brady et al. | |
| 7,033,487 B2 | | 4/2006 | O'Connor et al. | |
| 7,135,602 B1 | | 11/2006 | Le Van Mao | |
| 2004/0069684 A1 | * | 4/2004 | Tallman et al. | 208/161 |

OTHER PUBLICATIONS

Speight, et al.,"Refinery Processes—Survey" in Kirk-Othmer Encyclopedia of Chemical Technology, John Wiley and Sons, 1996.*
Barker, et al., "Petroleum" in Kirk-Othmer Encyclopedia of Chemical Technology, John Wiley and Sons, 2005, available on-line May 13, 2005.*
"UOP Fluid Catalytic Cracking (FCC) and Related Processes," Process Technology and Equipment, 2003, pp. 1-4, UOP LLC, Des Plaines, IL.

* cited by examiner

*Primary Examiner* — In Suk Bullock
*Assistant Examiner* — Bradley Etherton
(74) *Attorney, Agent, or Firm* — KBR IP Legal Dept.

(57) ABSTRACT

Systems and methods for producing and using one or more doped catalysts are provided. One or more coked-catalyst particles can be fluidized in the presence of one or more oxidants to provide a fluidized mixture. The coke from the one or more coked-catalyst particles can be removed to provide regenerated catalyst particles within the fluidized mixture. One or more doping agents can be distributed to the fluidized mixture, and the one or more doping agents can be deposited onto the surface of the regenerated catalyst particles to provide a regenerated, doped catalyst particle.

29 Claims, 2 Drawing Sheets

METHOD FOR ADJUSTING CATALYST ACTIVITY

BACKGROUND

1. Field

The present embodiments generally relate to systems and methods for adjusting the activity or selectivity of a catalyst. More particularly, embodiments of the present invention relate to systems and methods for selectively adjusting the activity or selectivity of a catalyst for hydrocarbon processing through an in-situ addition of one or more doping agents during regeneration of the catalyst.

2. Description of the Related Art

Hydrocarbon cracking is a method where under controlled temperature, pressure, and reaction conditions, one or more carbon-carbon bonds in a heavy molecular weight hydrocarbon can be broken (or "cracked") to form two or more lower molecular weight hydrocarbons or rearranged, with or without hydrogen transfer, to different molecules, including olefinic and aromatic compounds. Generally temperature, pressure and residence time within the cracker are adjusted to favor the production of desirable compounds. In fluidized catalytic crackers ("FCC"), a catalyst is employed to increase the yield of preferred lower molecular weight hydrocarbons, and to compensate for variations in hydrocarbon feedstock composition. Various additives or doping agents can be added to the catalyst to provide a doped catalyst where high performance or highly selective catalysts are desired.

Traditional production of doped FCC catalysts involves a multi-step process where the catalyst and the doping agent are uniformly dispersed within a solution. Heat is often applied to the solution to precipitate the catalyst. While a uniform, highly porous catalyst can thus be produced, the doping agent is dispersed more-or-less uniformly throughout the catalyst particle. Alternatively, the solid catalyst is dispersed in a solution containing the doping agent and dried. Since cracking occurs only on the exposed surfaces of the catalyst particle (hence the desirability of a highly porous catalyst), doping agent embedded deep within the catalyst matrix is unavailable to the cracking process. Where the supply of doping agent is limited, or where the doping agents are expensive or environmentally sensitive, the quantity of doping agent "lost" within the catalyst matrix may limit the overall availability of catalyst, may dramatically increase the cost of fresh catalyst, or may dramatically increase the cost of disposal for spent catalyst.

Where the composition of an incoming hydrocarbon feedstock is highly variable, it may be desirable to adjust the doping agent type or concentration to maintain a consistent finished product. With a traditional catalyst, since the doping agent remains embedded within the catalyst matrix, changing catalysts and/or doping agents in response to feedstock variations often requires complete replacement of the catalyst charge in the system. Such replacements are inefficient and costly, particularly as the variability of hydrocarbon feedstocks increases due to the frequent sourcing from multiple production regions scattered across wide geographic areas.

Given increasing reliance on the cracking of marginal quality crude oil feedstocks having highly variable compositions, there is a need therefore, for a method and process for rapidly adjusting the quantity or composition of doping agents used in FCC catalysts.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Systems and methods for producing and using one or more doped catalysts are provided. One or more coked-catalyst particles can be fluidized in the presence of one or more oxidants to provide a fluidized mixture. The coke from the one or more coked-catalyst particles can be removed to provide regenerated catalyst particles within the fluidized mixture. One or more doping agents can be distributed to the fluidized mixture, and the one or more doping agents can be deposited onto the surface of the regenerated catalyst particles to provide a regenerated, doped catalyst particle.

Figure 1:
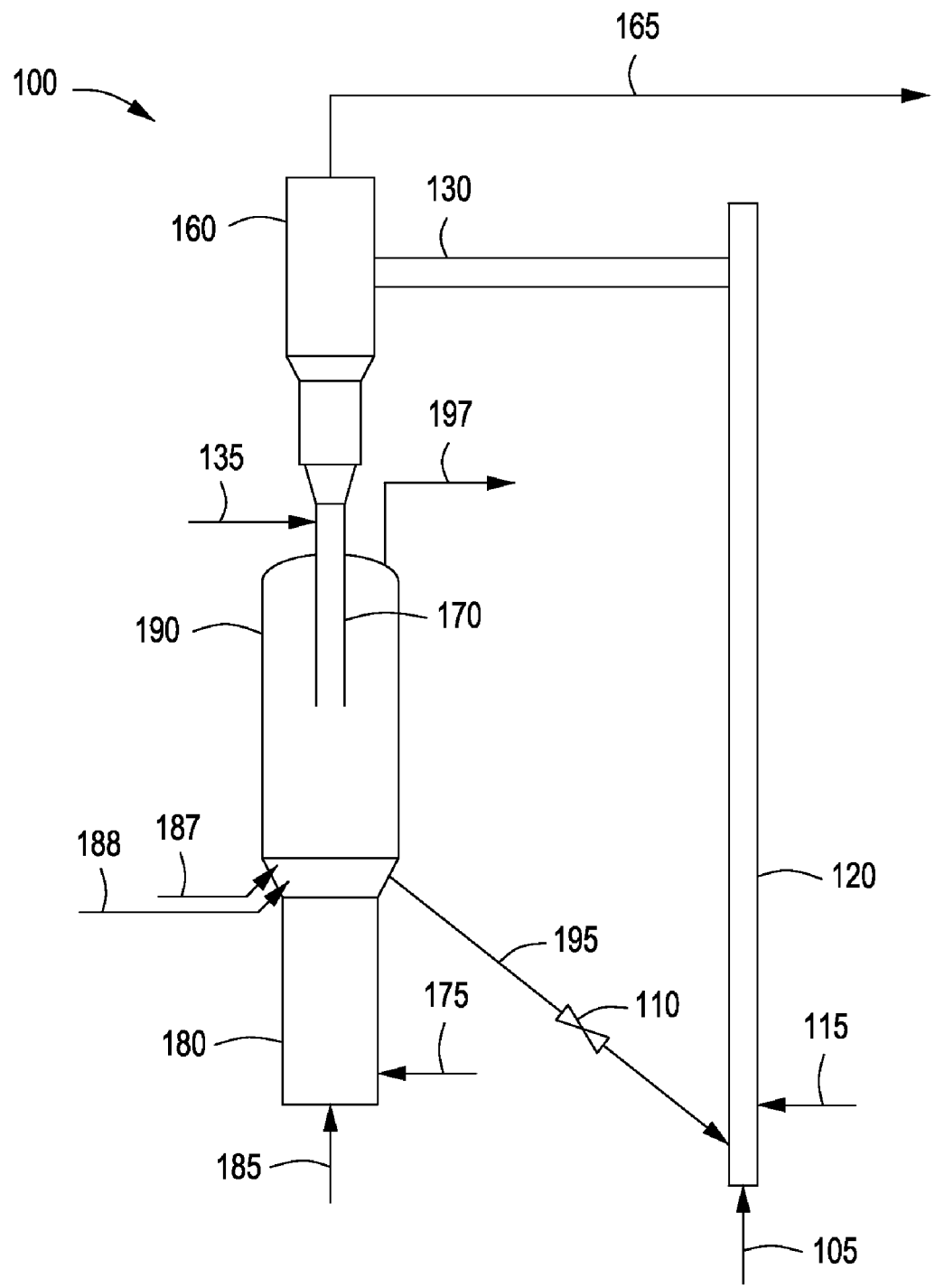
FIG. 1 depicts an illustrative system for regenerating and doping catalyst, according to one or more embodiments described.

With reference to the figures, FIG. 1 depicts an illustrative system 100 for regenerating and doping catalyst, according to one or more embodiments. In one or more embodiments, the system 100 can be a fluidized catalytic cracker ("FCC") or other suitable system having one or more risers 120, ducts 130, separation zones 160, combustion zones 180, and regeneration zones 190. In one or more embodiments, steam via line 105, a hydrocarbon feed via line 115 and a doped catalyst via line 195 can be introduced to the one or more risers 120, forming a fluidized mixture ("reaction mixture") therein. The steam via line 105 and the doped catalyst via line 195 can be fed separately to the riser 120 as shown in FIG. 1, or the steam and the doped catalyst can be mixed and fed together as a mixture to the riser 120.

In one or more embodiments, heat in the riser 120 provided by the steam via line 105 and the doped catalyst via line 195 can vaporize the hydrocarbon feed via line 115 entering the riser 120, and forming a mixture ("reaction mixture") therein. In one or more embodiments, supplemental heat and/or firing can be provided to the one or more risers 120 using waste heat provided from the one or more combustion zones 180 and/or regeneration zones 190. Within the riser 120, the hydrocarbons within the reaction mixture can be substantially cracked into one or more hydrocarbons and hydrocarbon by-products to provide a first product mixture. In one or more embodiments, at least a portion of the hydrocarbon by-products present in the riser 120 can deposit on the surface of the catalyst particles, forming coked-catalyst particles. Thus, the first product mixture exiting the riser 120 can contain coked-catalyst particles suspended in gaseous hydrocarbons, hydrocarbon by-products, steam, and other inerts.

In one or more embodiments, the velocity of the reaction mixture flowing through the riser 120 can range from about 3 m/sec (10 ft/sec) to about 27 m/sec (90 ft/sec), about 6.1 m/sec (20 ft/sec) to about 24.4 m/sec (80 ft/sec), or about 9.1 m/sec (30 ft/sec) to about 21.3 m/sec (70 ft/sec). In one or more embodiments, the residence time of the reaction mixture in the riser 120 can be less than about 20 seconds, about 10 seconds, about 8 seconds, about 4 seconds, or about 2 seconds.

In one or more embodiments, the first product mixture can flow, via the duct 130, to the one or more separation zones 160 where the coked-catalyst particles can be separated from the gaseous hydrocarbons, steam, and inerts. The separation zone 160 can be a section of the system 100 having a larger cross-sectional area than either the riser 120 or the duct 130 to reduce the velocity of the gas, allowing the heavier coked-catalyst particles to separate from one or more gaseous hydrocarbons, steam, and inerts. In one or more embodiments, a steam purge can be added via line 135 to the separation zone 160 to assist in separating the gaseous hydrocarbons from the coked-catalyst particles, i.e. stripping the gaseous hydrocarbons from the solids.

In one or more embodiments, the gaseous hydrocarbons can be removed from the separation zone 160 via line 165. The gaseous hydrocarbons in line 165 can be further processed, such as by dehydrating or fractionating to provide one or more finished products including, but not limited to, one or more olefins, paraffins, aromatics, mixtures thereof, derivatives thereof, and/or combinations thereof. The solids, i.e. coked-catalyst particles, can free fall through the separation zone discharge 170 toward the combustion and regeneration zone 180, 190.

In one or more embodiments, within the combustion and regeneration zones 180, 190, the coked-catalyst particles can be combined with one or more oxidizing agents introduced via line 185 including, but not limited to air, oxygen, and/or oxygen enriched air. The one or more oxidizing agents can react with the carbonaceous matter on the coked-catalyst particles to combust or otherwise burn the carbon ("coke") off the surface of the catalyst particle. In one or more embodiments, fresh, unused, catalyst can be added via line 175 to the combustion zone 180, and/or regeneration zones 190 (not shown). The removal of the coke from the surface of the catalyst particle can re-expose the reactive surfaces of the catalyst, thereby "regenerating" the catalyst particle, permitting its reuse. Combustion by-products, such as carbon monoxide and carbon dioxide, can be removed from the system 100 as a waste gas via line 197.

In one or more embodiments, within the regeneration zone 190 a fluidized mixture, containing substantially de-coked (i.e. "clean") catalyst particles, carbon monoxide, carbon dioxide, and the one or more oxidizing agents can be combined with one or more doping agents introduced via line 187. The dispersal and deposition of the one or more doping agents on the regenerated catalyst can be enhanced by the high temperature and turbulence present in the regeneration zone 190. In one or more embodiments, the regeneration zone 190 can operate at a temperature range of from about 480° C. (900° F.) to about 900° C. (1,650° F.); from about 590° C. (1,100° F.) to about 815° C. (1,500° F.); or from about 650° C. (1,200° F.) to about 815° C. (1,500° F.).

In one or more embodiments, the one or more doping agents can be mixed with a supplemental fuel, for example natural gas, and introduced to the regeneration zone 190 via line 188. The use of supplemental fuel can provide additional heat within the regeneration zone 190, further enhancing the regeneration of the coked-catalyst particles therein.

In one or more embodiments, the turbulence within the regeneration zone 190 can assist the even dispersion of the one or more doping agents within the fluidized mixture, increasing the contact between the one or more doping agents with the reactive surfaces on the regenerated catalyst. In contrast, the one or more doping agents in a traditional, homogeneously doped, catalyst are dispersed within the catalyst particles. Consequently, less doping agent can be used to achieve the same concentration of doping agent on the surface of the regenerated catalyst particle. Also, changing doping agents in response to changing process conditions and/or hydrocarbon feed composition can be more readily achieved since little or no entrained doping agent exists within the catalyst particle, i.e. the interior matrix of the catalyst particle. For example, the doping agent can be changed simply by changing the type and/or composition of the doping agent added to the regeneration zone 180.

In one or more embodiments, the selection of an appropriate doping agent or additive or blend of two or more doping agents or additives can be based upon the composition of the incoming hydrocarbon feed via line 115, and/or desired gaseous hydrocarbons in the first product exiting the catalytic cracker via line 165. For example, the addition of a class 2 doping agent such as magnesium or barium can preferentially increase the production of ethylene in the first product in line 165. The addition of a class 13 doping agent such as gallium can result in the increased production of aromatic hydrocarbons in the first product in line 165. The addition of class 8, 9, or 10 doping agents such as ruthenium, rhodium or palladium can preferentially increase the production of propylene in the first product in line 165.

In one or more embodiments, doped catalyst particles, containing regenerated catalyst particles with one or more doping agents or additives can be returned to the one or more risers 120 via line 195. In one or more embodiments, the flow of regenerated catalyst from the regeneration zone 190 can be controlled using one or more valves 110, which can be manually or automatically adjusted or controlled based upon parameters derived from process temperatures, pressures, flows and/or other process conditions. In one or more embodiments, at least 90% wt, at least 95% wt, at least 99% wt, at least 99.99% wt, at least 99.9975% wt, or at least 99.999% wt of the total doped catalyst originally introduced to the riser 120 via line 195 can be regenerated, doped with one or more doping agents, and recycled back to the riser 120.

In one or more embodiments, the hydrocarbon feed in line 115 can include, but is not limited to, mixed olefins, paraffins, mixtures thereof, and/or any combination thereof. In one or more embodiments, the hydrocarbon feed can originate from a refinery. For example, the hydrocarbon feed can be a gas mixture resulting from the distillation of crude oil. In one or more embodiments, the hydrocarbon feed can contain hydrocarbon compounds containing 11 or fewer carbon atoms. In one or more embodiments, the hydrocarbon feed can include from about 0.1% vol to 5% vol methane; from about 0.1% vol to about 10% vol ethane; from about 0.1% vol to about 30% vol propane. In one or more embodiments, the hydrocarbon feed can contain from about 0% vol to about 35% vol butane; and from about 0% vol to about 20% vol pentane and heavier hydrocarbons. In one or more embodiments, the hydrocarbon feed can include at least 60% wt $C_2$-$C_{11}$ olefins and paraffin.

In one or more embodiments, the hydrocarbon feed introduced via line 115 can be pre-heated prior to introduction to the riser 120. Although not shown in FIG. 1, a regenerative heat exchanger using waste process heat can be used to pre-heat the hydrocarbon feed. In one or more embodiments, the temperature of the hydrocarbon feed can range from about 370° C. (700° F.) to about 790° C. (1,450° F.), about 425° C. (800° F.) to about 700° C. (1,300° F.), or about 480° C. (900° F.) to about 700° C. (1,300° F.). In one or more embodiments, the pressure of the hydrocarbon feed can range from about 100 kPa (0 psig) to about 3,450 kPa (485 psig), about 100 kPa (0 psig) to about 2,750 kPa (385 psig), or about 100 kPa (0 psig) to about 350 kPa (35 psig).

In one or more embodiments, the hydrocarbon feed introduced via line 115 can be partially or completely vaporized prior to introduction to the one or more risers 120. In one or more embodiments, the hydrocarbon feed can be at least about 10 vol % to about 100 vol %; about 20 vol % to about 60 vol %; about 30 vol % to about 60 vol %; about 40 vol % to about 60 vol %; or about 50 vol % to about 60 vol % vaporized. In one or more embodiments, the hydrocarbon feed can be at least about 70 vol % to about 100 vol %; about 80 vol % to about 100 vol %; or about 90 vol % to about 100 vol % vaporized. In one or more embodiments, the hydrocarbon feed can be a minimum of 80% wt vaporized; 85% wt vaporized; 90% wt vaporized; 95% wt vaporized; or about 99% wt vaporized prior to introduction to the riser 120. In one or more embodiments, within the riser 120, pressure and temperature can be adjusted either manually or automatically to compensate for variations in hydrocarbon feed composition and to maximize the yield of preferred hydrocarbons obtained by cracking the hydrocarbon feed in the presence of the one or more doped catalysts.

In one or more embodiments, the steam introduced via line 105 to the one or more risers 120 can be saturated. The pressure of the saturated steam can be a minimum of about 1,000 kPa (130 psig), about 2,000 kPa (275 psig), about 4,000 kPa (565 psig), or about 6,000 kPa (855 psig). In one or more embodiments, the pressure of the saturated steam can range from about 100 kPa (0 psig) to about 8,300 kPa (1,190 psig); about 100 kPa (0 psig) to about 4,000 kPa (565 psig); or about 100 kPa (0 psig) to about 2,000 kPa (275 psig).

In one or more embodiments, the steam introduced via line 105 to the one or more risers 120 can be superheated. In one or more embodiments, where superheated steam is used, the pressure of the superheated steam can be a minimum of about 1,000 kPa (130 psig), about 2,000 kPa (276 psig), about 4,000 kPa (565 psig), or about 6,000 kPa (855 psig). In one or more embodiments, the pressure of the superheated steam can range from about 100 kPa (0 psig) to about 8,300 kPa (1,190 psig); about 100 kPa (0 psig) to about 4,000 kPa (565 psig); or about 100 kPa (0 psig) to about 2,000 kPa (275 psig). In one or more embodiments, the temperature of the superheated steam can be a minimum of about 200° C. (400° F.), about 230° C. (450° F.), about 260° C. (500° F.), or about 290° C. (550° F.).

In one or more embodiments, the steam can be introduced via line 105 to the riser 120 at a rate proportionate to the hydrocarbon feed rate via line 115. In one or more embodiments, the steam-to-hydrocarbon feed weight ratio can range from about 1:20 to about 50:1; from about 1:20 to about 20:1; or from about 1:10 to about 20:1.

In one or more embodiments, the catalyst can include, but is not limited to one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), or high activity zeolite catalysts. In one or more embodiments, the catalyst-to-oil weight ratio can range from about 5:1 to about 70:1; from about 8:1 to about 25:1; or from about 12:1 to about 18:1. In one or more embodiments, the temperature of the doped catalyst, prior to introduction to the riser 120, can range from about 200° C. (400° F.) to about 815° C. (1,500° F.); about 200° C. (400° F.) to about 760° C. (1,400° F.); or about 200° C. (400° F.) to about 675° C. (1,250° F.).

In one or more embodiments, the first product in line 165 can include from about 5% wt to about 30% wt $C_2$; about 5% wt to about 60% wt $C_3$; about 5% wt to about 40% wt $C_4$; about 5% wt to about 50% wt $C_5$ and heavier hydrocarbons. In one or more embodiments, the temperature of the first product in line 165 can range from about 425° C. (800° F.) to about 815° C. (1,500° F.); about 450° C. (850° F.) to about 760° C. (1,400° F.); or about 480° C. (900° F.) to about 730° C. (1,350° F.).

Figure 2:
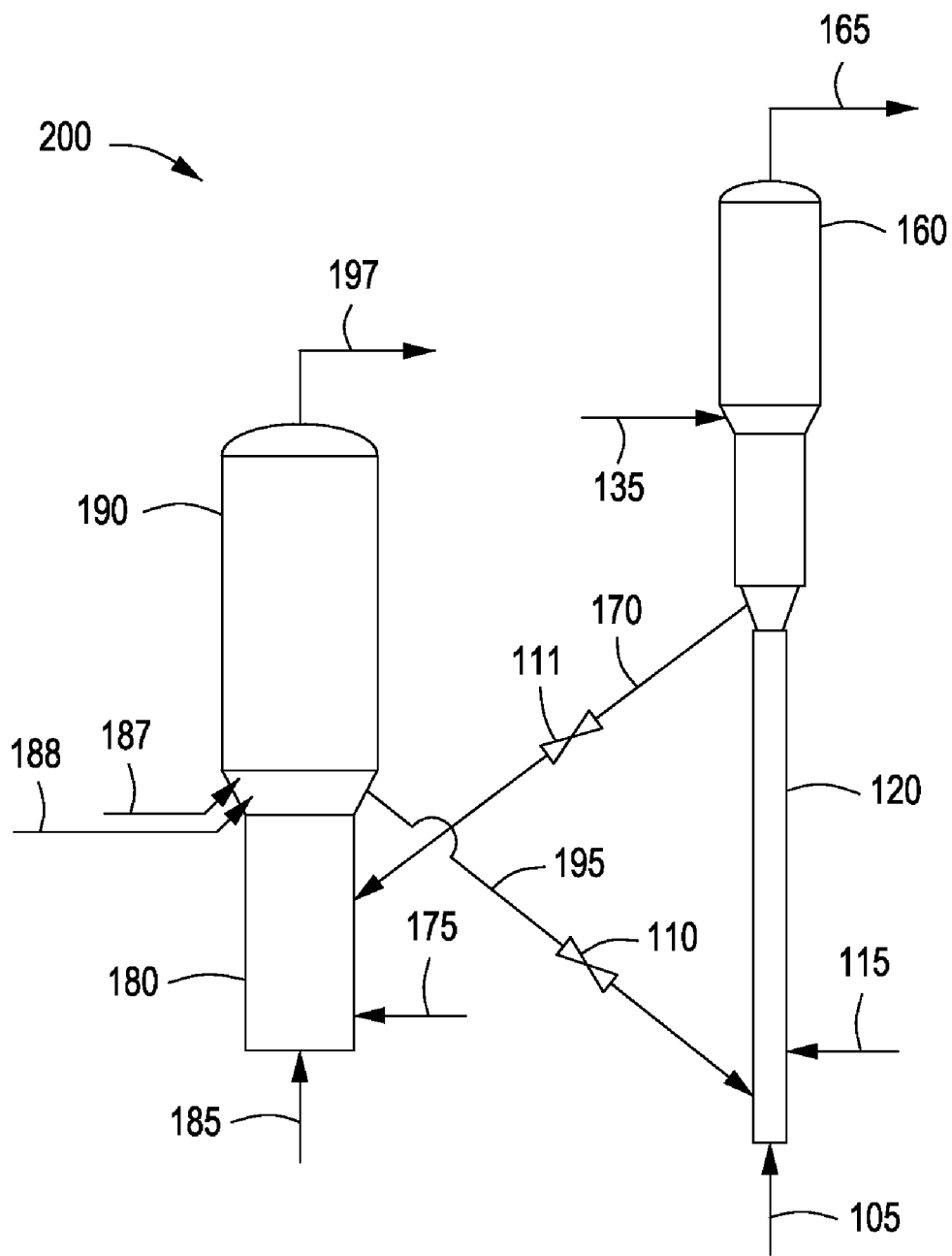
FIG. 2 depicts another illustrative system for regenerating and doping catalyst, according to one or more embodiments described.

FIG. 2 depicts another illustrative system 200 for regenerating and doping catalyst according to one or more embodiments. In one or more embodiments, the system 200 can include one or more risers 120, separation zones 160, combustion zones 180, and regeneration zones 190. In one or more embodiments, the separation zone 160 can be disposed above the riser 120 as depicted in FIG. 2. In one or more embodiments, the separation zone 160 can include a separation zone discharge 170 which can provide fluid communication between the separation zone 160 and one or more combustion zones 180. The separation zone discharge 170 can include one or more valves 111 to manually or automatically adjust or control the flow of coked-catalyst particles to the combustion zone 180 based on parameters derived from process temperatures, pressures, flows, and/or other process conditions.

As described above, the hydrocarbon feed via line 115, steam via line 105 and the one or more doped catalysts via line 195 can be introduced to the riser 120, forming the reaction mixture therein. In one or more embodiments, at least a portion of the hydrocarbons present in the reaction mixture can crack or otherwise react to form one or more gaseous hydrocarbons and one or more hydrocarbon byproducts. In the reaction mixture within the riser 120, at least a portion of the hydrocarbon by-products can deposit onto the doped catalyst particles, forming coked-catalyst particles. In one or more embodiments, the first product mixture exiting the riser 120 can contain coked-catalyst particles suspended in gaseous hydrocarbons, hydrocarbon by-products, steam, and other inerts.

In one or more embodiments, the first product mixture can be introduced to the separation zone 160 wherein the coked-catalyst particles can be separated from the gaseous hydrocarbons. The gaseous hydrocarbons can be removed via line 165 from the separation zone 160, while the separated coked-catalyst particles can fall through the separation zone 160, and into the separation zone discharge 170. In one or more embodiments, one or more valves 111 can be located within the separation zone discharge 170 to control the flow of separated coked-catalyst particles from the separation zone 160 to the combustion zone 180.

In one or more embodiments, fresh, unused, catalyst can be added via line 175 to the combustion zone 180, and/or regeneration zone 190 (not shown). In one or more embodiments, within the combustion zone 180 the coked-catalyst particles can be mixed with one or more oxidants, introduced via line 185, and combusted to remove the coke from the surface of the catalyst particles, forming regenerated catalyst particles.

The regenerated catalyst particles in the combustion zone 180 can enter the regeneration zone 190 where the one or more doping agents can be added either neat via line 187, or mixed with a supplemental fuel via line 188. The one or more doping agents can be dispersed across the surface of the catalyst particles, thereby forming doped catalyst particles which can be recycled from the regeneration zone 190 to the riser 120 via line 195.

EXAMPLE

The foregoing discussion can be further described with reference to the following non-limiting example. In the examples below, a gallium-containing doping agent, specifically dry gallium nitrate, was added to an FCC regeneration zone. Heptene was used for the hydrocarbon feed. The cracking operation, using the gallium doped catalyst, was in operation for approximately two (2) days. Catalyst inventory was 4,000 g and the catalyst rate was 20,000 g/hr. The hydrocarbon feed rate was maintained at about 1,000 g/hr. The hydrocarbon partial pressure was about 25 pounds per square inch absolute ("psia"). The gallium dosage rate was maintained at an equivalent of 30 g as gallium nitrate or 0.2% as gallium on a ZSM-5 catalyst. The results of the gallium additive to the regenerator compared to an identical process without the gallium addition are summarized in Table 1 below.

TABLE 1

Results of Gallium Additive to the Regenerator

| | Without dopant | With dopant |
|---|---|---|
| Liquid Yield (g/hr) | 307 | 375 |
| Liquid P/I/O/N/A | 14/5/35/4/40 | 12/4/32/3/48 |
| Ethylene Yield (wt %) | 11.9 | 13.5 |
| Propylene Yield (wt %) | 32.7 | 31.5 |
| Aromatic Yield (wt %) | 12.3 | 18.0 |

The term "P/I/O/N/A," as used in Table 1, refers to the relative percentage (by weight) of the following components: paraffins (P), isoparaffins (I), olefins (O), naphthalenes (N), and aromatics (A).

As shown in Table 1, the ethylene yield increased by about 10%, a significant amount in a price competitive market, and the propylene yield was about the same. Surprisingly, however, the aromatic yield increased by about 46%.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for doping hydrocarbon cracking catalyst, comprising:
    fluidizing one or more coked-catalyst particles in the presence of one or more oxidants to provide a fluidized mixture;
    removing at least a portion of the coke from the one or more coked-catalyst particles to provide regenerated catalyst particles within the fluidized mixture;
    distributing one or more doping agents to the fluidized mixture;
    depositing the one or more doping agents onto a surface of the regenerated catalyst particles to provide one or more doped catalyst particles; and
    cracking a hydrocarbon feed in the presence of the one or more doped catalyst particles to provide a hydrocarbon product, wherein;
    the hydrocarbon product comprises ethylene, propylene, and aromatic hydrocarbons,
    an amount of at least one of ethylene and propylene in the hydrocarbon product is at least 5 wt % based on a weight of the hydrocarbon feed, and
    cracking the hydrocarbon feed cokes the one or more doped catalyst particles to provide the one or more coked-catalyst particles for the fluidized mixture;
    wherein the one or more doping agents comprise gallium and at least one of magnesium, barium, ruthenium, rhodium, and palladium.

2. The method of claim 1, wherein the amount of at least one of ethylene and propylene in the hydrocarbon product is at least 10 wt % based on the weight of the hydrocarbon feed.

3. The method of claim 1, further comprising increasing a temperature of the fluidized mixture above 480° C. prior to distributing the one or more doping agents.

4. The method of claim 1, wherein the one or more oxidants comprises air, oxygen, oxygen enriched air, or mixtures thereof.

5. The method of claim 1, wherein the hydrocarbon cracking catalyst comprises one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

6. The method of claim 1, wherein the hydrocarbon product comprises at least 10 wt % ethylene and at least 15 wt % aromatic hydrocarbons based on a weight of the hydrocarbon feed.

7. The method of claim 1, wherein a combined amount of ethylene and aromatic hydrocarbons in the hydrocarbon product is at least 25 wt % based on a weight of the hydrocarbon feed, and wherein the amount of propylene in the hydrocarbon product is at least 25 wt % based on the weight of the hydrocarbon feed.

8. The method of claim 1, wherein at least a portion of the hydrocarbon product comprises liquid hydrocarbons, wherein the liquid hydrocarbons comprise paraffins, isoparaffins, olefins, naphthalenes, and aromatics, and wherein an amount of the aromatics in the liquid portion is greater than 45 wt % based on a weight of the liquid hydrocarbons.

9. The method of claim 1, wherein the doped catalyst particles contain about 0.2 wt % of the one or more doping agents based on a weight of the doped catalyst particles.

10. The method of claim 1, wherein the one or more doping agents is distributed to the fluidized mixture in the form of a mixture comprising the one or more doping agents and a supplemental fuel.

11. The method of claim 1, wherein the doped catalyst particles produce about 10% or more ethylene in the hydrocarbon product relative to the regenerated catalyst particles without the one or more doping agents deposited thereon.

12. The method of claim 1, wherein the doped catalyst particles produce about 40% or more aromatic hydrocarbons in the hydrocarbon product relative to the regenerated catalyst particles without the one or more doping agents deposited thereon.

13. The method of claim 1, wherein the one or more doping agents increase an amount of ethylene and an amount of aromatic hydrocarbons and decrease an amount of propylene in the hydrocarbon product relative to the regenerated catalyst particles without the one or more doping agents deposited thereon.

14. The method of claim 1, wherein the hydrocarbon feed comprises at least 60 wt % olefins and paraffins.

15. The method of claim 1, wherein the hydrocarbon product comprises at least 10 wt % ethylene, at least 25 wt % propylene, and at least 15 wt % aromatic hydrocarbons based on a weight of the hydrocarbon feed.

16. The method of claim 1, wherein the one or more doping agents comprise gallium nitrate.

17. The method of claim 1, wherein the hydrocarbon cracking catalyst comprises Socony Mobil #5 zeolite (ZSM-5).

18. A method for catalytically cracking one or more hydrocarbons, comprising:
fluidizing a hydrocarbon in the presence of one or more doped catalyst particles to provide a fluidized reaction mixture;
selectively cracking the hydrocarbon to provide one or more gaseous hydrocarbons, one or more hydrocarbon by-products, and coked-catalyst particles;
selectively separating the one or more gaseous hydrocarbons from the coked-catalyst particles to provide a hydrocarbon product comprising ethylene, propylene, and aromatic hydrocarbons, wherein an amount of at least one of ethylene and propylene in the hydrocarbon product is at least 5 wt % based on a weight of the hydrocarbon feed;
fluidizing the coked-catalyst particles with one or more oxidants;
removing coke from the coked-catalyst particles to provide fluidized regenerated catalyst particles;
introducing one or more doping agents to the fluidized regenerated catalyst particles to provide the one or more doped catalyst particles; and
returning the one or more doped catalyst particles to the fluidized reaction mixture;
wherein the one or more doping agents comprise gallium and at least one of magnesium, barium, ruthenium, rhodium, and palladium.

19. The method of claim 18, further comprising increasing a temperature of the fluidized mixture above 480° C. prior to introducing the one or more doping agents.

20. The method of claim 18, wherein the one or more oxidants comprises air, oxygen, oxygen enriched air, or mixtures thereof.

21. The method of claim 18, wherein the catalyst comprises zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

22. The method of claim 18, wherein the hydrocarbon comprises one or more hydrocarbons having 11 or fewer carbon atoms.

23. The method of claim 18, wherein the one or more doping agents comprise gallium nitrate.

24. A method for catalytically cracking one or more hydrocarbons, comprising:
fluidizing a hydrocarbon in the presence of one or more doped catalyst particles to provide a fluidized reaction mixture;
selectively cracking the hydrocarbon in the presence of the one or more doped catalyst particles to provide one or more gaseous hydrocarbons, one or more hydrocarbon by-products, and coked-catalyst particles;
selectively separating the one or more gaseous hydrocarbons from the coked-catalyst particles to provide a hydrocarbon product comprising ethylene, propylene, and aromatic hydrocarbons, and wherein an amount of at least one of ethylene and propylene in the hydrocarbon product is at least 5 wt % based on a weight of the hydrocarbon feed;
fluidizing the coked-catalyst particles;
removing coke from the coked-catalyst particles to provide regenerated catalyst particles;
selecting one or more doping agents based at least in part on a composition of the hydrocarbon feed;
introducing the one or more selected doping agents to the regenerated catalyst particles to provide the one or more doped catalyst particles; and
returning the one or more doped catalyst particles to the fluidized reaction mixture;
wherein the one or more doping agents comprise gallium and at least one of magnesium barium, ruthenium, rhodium and palladium.

25. The method of claim 24, further comprising increasing a temperature of the fluidized mixture above 480° C. prior to introducing the one or more selected doping agents.

26. The method of claim 24, wherein the coked-catalyst particles are fluidized in the presence of one or more oxidants that comprises air, oxygen, oxygen enriched air, or mixtures thereof.

27. The method of claim 24, wherein the catalyst comprises zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

28. The method of claim 24, wherein the hydrocarbon comprises one or more hydrocarbons having 11 or fewer carbon atoms.

29. The method of claim 24, wherein the one or more doping agents comprise gallium nitrate.

* * * * *